(12) United States Patent
Shimada et al.

(10) Patent No.: US 8,734,431 B2
(45) Date of Patent: May 27, 2014

(54) REMOTE CONTROL SYSTEM

(75) Inventors: Jun-ichi Shimada, Kyoto (JP); Atsushi Nishikawa, Ikoma (JP)

(73) Assignee: Yanchers Inc., Kyoto (JP)

( * ) Notice: Subject to any disclaimer, the term of this patent is extended or adjusted under 35 U.S.C. 154(b) by 960 days.

(21) Appl. No.: 12/308,380

(22) PCT Filed: Jun. 15, 2007

(86) PCT No.: PCT/JP2007/062147
§ 371 (c)(1),
(2), (4) Date: Mar. 5, 2009

(87) PCT Pub. No.: WO2007/145327
PCT Pub. Date: Dec. 21, 2007

(65) Prior Publication Data
US 2009/0187288 A1    Jul. 23, 2009

(30) Foreign Application Priority Data
Jun. 15, 2006   (JP) .................................. 2006-166381

(51) Int. Cl.
*G05D 1/12*    (2006.01)

(52) U.S. Cl.
USPC ............................................. 606/1; 600/427

(58) Field of Classification Search
USPC ...................................... 600/427; 606/1, 130
See application file for complete search history.

(56) References Cited

U.S. PATENT DOCUMENTS

| 6,334,067 | B1 * | 12/2001 | Brabrand ...................... | 600/427 |
| 6,380,958 | B1 * | 4/2002 | Guendel et al. ................ | 715/848 |
| 2004/0171924 | A1 * | 9/2004 | Mire et al. .................... | 600/407 |

FOREIGN PATENT DOCUMENTS

| JP | A-2-198784 | 8/1990 |
| JP | A-6-30896 | 2/1994 |
| JP | A-8-215205 | 8/1996 |
| JP | A-2002-253574 | 9/2002 |
| JP | A-2003-52716 | 2/2003 |

OTHER PUBLICATIONS

Krupa et al., "Autonomous 3-D Positioning of Surgical Instruments in Robotized Laparoscopic Surgery Using Visual Servoing," *IEEE Transactions on Robotics and Automation*, vol. 19, No. 5, Oct. 2003, pp. 842-853.
May 29, 2012 Office Action issued in Japanese Patent Application No. 2008-521275 (with translation).
Nov. 20, 2012 Japanese Office Action issued in Japanese Patent Application No. 2008-521275 (with translation).

* cited by examiner

*Primary Examiner* — Bill Thomson
*Assistant Examiner* — Jeffrey Lipitz
(74) *Attorney, Agent, or Firm* — Oliff PLC

(57) ABSTRACT

A remote control system capable of precise operations or treatments in which the visual recognition and operation portions are as close to each other as possible, including: a) an imaging device for taking an image of the object; b) a manipulation tool having at its tip an illuminator for casting a spot light onto the object; c) a driver for changing the position of the manipulation tool; d) an external display unit for displaying an image; e) an input unit for allowing an operator to specify a position corresponding to the display of the external display unit; f) a distance calculator for calculating the distance between the position specified through the input unit and the position of the spot light cast from the illuminator onto the object; and g) a controller for controlling, based on the aforementioned distance, the driver so as to bring the tip of the manipulation tool closer to the specified position.

20 Claims, 4 Drawing Sheets

REMOTE CONTROL SYSTEM

TECHNICAL FIELD

The present invention relates to a remote control system for performing an operation on an object located within a space beyond a partition. This remote control system can suitably be applied to a surgery system that is least invasive to the human body and yet capable of precise operations.

BACKGROUND ART

For many years, surgical treatments (operations) for human beings have relied on a physician visually examining a target portion and performing necessary treatments, such as retracting or resecting the target portion, by manually utilizing a scalpel or other surgical tools.

However, the targets of operations have been smaller in size and finer in structure in accordance with the accumulation of biological and anatomical information relating to the target organs and the improvement of the medical techniques. Meanwhile, the progress in electronics has enabled the creation of an imaging system that is smaller in size yet higher in resolution, with a satisfactory level of color-reproducing capability that allows the system to be used in the actual treatments. As a result, endoscopic surgical operations have been widely performed in recent years, in which an image of the inside of the body taken through optical fibers is displayed on a large screen and a physician manipulates a surgical tool while watching the screen.

Efforts have also been made in searching for a method of remotely manipulating a tool by means of a manipulator, and a variety of specific methods have been proposed. For example, Patent Document 1 discloses a system for driving a manipulator having a built-in endoscope. In this system, the manipulator is operated through a control stick or voice recognition unit.

Patent Document 2 discloses a point-lock system in which an insertion hole formed in a body wall is utilized as the supporting point for a rod-shaped manipulator to minimize the invasion to a patient. In this system, an operator wearing a face mounted display (FMD) drives a treating manipulator through an operation input device while visually checking an image projected on the FMD. The motion and position of a viewing manipulator are controlled according to the motion of the physician's head detected by a three-dimensional digitizer provided in the FMD.

Patent Document 3 discloses a system with a manipulator support mechanism especially designed to reduce the burden on the operator. Accordingly, in this system, the operator needs to directly operate the manipulator. The endoscopic image is displayed on an external screen.

Non-Patent Document 1 discloses a method of controlling a surgical tool having three light-emitting points on the side of its tip. Based on an image of these three points, the distance between the internal irradiation point (laser spot) of the laser light emitted from the tip of the surgical tool and the tip of the same tool is determined, and the surgical tool is controlled so that the distance will be at a predetermined value.

Patent Document 1: Japanese Unexamined Patent Application Publication No. H06-030896
Patent Document 2: Japanese Unexamined Patent Application Publication No. H08-215205
Patent Document 3: Japanese Unexamined Patent Application Publication No. 2003-052716
Non-Patent Document 1: A. Krupa, et al., "Autonomous 3-D Positioning of Surgical Instruments in Robotized Laparoscopic Surgery Using Visual Servoing", *IEEE Trans. on Robotics and Automation*, Vol. 19 (2003), No. 5, pp. 842-853

DISCLOSURE OF THE INVENTION

Problem to be Solved by the Invention

As described in the previous section, the manipulators in the conventional surgery systems are operated directly by an operator (e.g. practitioner or physician) (Patent Document 3) or indirectly through an operation input device (Patent Document 1 or 2). The endoscopic image of the surgery site is displayed on an external screen (Patent Document 1 or 3) or provided through an FMD or HMD (head mounted display) (Patent Document 2).

However, the FMD and HMD either totally or partially prevent the wearer from visually checking the surroundings. Medical operations are normally performed by a team of members, in which the practitioners (e.g. physicians) must clearly be aware of the surroundings; otherwise, the communication among the team members will be inadequate, which will prevent the operation from being smoothly performed.

As compared to the conventional action of simultaneously watching and manipulating the surgical tool, the action of operating an operation input device while watching an external screen is unnatural in that the visual recognition portion is separated from the operation portion, which impedes the operation from being performed with adequate precision.

Non-Patent Document 1 deals with the process of bringing the surgical tool to a point at a predetermined distance from the surface of the target organ. After that process, the operator is expected to perform an operation by manipulating the surgical tool manually or through the operation input device while watching an external screen.

The situation where the operator performs some operation on an object without visually checking the object may also occur in some remote control systems other than the surgery system. For example, if the object must be worked in an environment free from oxygen, water, dust and so on, the operator may place the object in a container from which the aforementioned substances have been removed, and then remotely manipulate a working tool from outside the container. If the operator is separated from the object in this manner by the wall of a container or the like and hence cannot fully check the object visually, the same problem may arise as in the previously described surgery system. This problem can also occur, for example, if the operator is at a remote place from the object, if the object is too small to be visible to the unaided eye, or if a microstructure that cannot be checked with the unaided eye must be created.

Thus, the problem to be solved by the present invention is to provide a remote control system, such as a surgery system, in which the visual recognition portion and the operation portion are as close to each other as possible for natural actions, and which is capable of precise operations.

Means for Solving the Problems

To solve the previously described problem, the present invention provides a remote control system for performing an operation on an object, which is characterized by comprising:
a) an imaging device for taking an image of the object;
b) a manipulation tool having, at the tip thereof, an illuminator for casting a spot light onto the object;
c) a driver for changing the position of the manipulation tool;

d) an external display unit for displaying an image taken by the imaging device;

e) an input unit for allowing an operator to specify a position corresponding to the display of the external display unit;

f) a distance calculator for calculating the distance between the position specified through the input unit and the position of the spot light cast from the illuminator on the object; and g) a controller for controlling, based on the aforementioned distance, the driver so as to bring the tip of the manipulation tool closer to the specified position.

The controller may also have the function of moving a surgical tool so as to decrease the aforementioned distance, and then controlling the driver so as to bring the tip of the surgical tool closer to the specified position after the aforementioned distance has been equal to or smaller than a predetermined value.

The remote control system according to the present invention can be suitably used in the case of performing an operation on an object located within a space beyond a partition. In that case, the remote control system is characterized by comprising:

a) an imaging device for taking an image of the object;

b) a rod-shaped manipulation tool having, at the tip thereof, an illuminator for casting a spot light, the manipulation tool being designed to be inserted through a hole provided in the partition;

c) a driver for changing the position of the manipulation tool;

d) an external display unit for displaying an image taken by the imaging device;

e) an input unit for allowing an operator to specify a position corresponding to the display of the external display unit;

f) a distance calculator for calculating the distance between the position specified through the input unit and the position of the spot light cast from the illuminator on the object; and g) a controller for controlling, based on the aforementioned distance, the driver so as to bring the tip of the manipulation tool closer to the specified position.

In the case where the partition is present, the controller may have the function of controlling the driver so as to:

rotate the manipulation tool about the hole so as to decrease the aforementioned distance; and move the manipulation tool in the axial direction thereof after the aforementioned distance has been equal to or smaller than a predetermined value.

The controller may further have the function of controlling the driver so that the aforementioned distance is maintained within a range equal to or smaller than the predetermined value when the specified position is moved. This function can be implemented regardless of the presence or absence of the partition.

The remote control system according to the present invention can be used as a surgery system by using a surgical tool as the manipulation tool. In that case, the object corresponds to the affected area of a patient. If the system is used in the case where the partition is present, the partition corresponds to the body wall of the patient.

Effects of the Invention

In the remote control system (including the surgery system) according to the present invention, when an operator (practitioner) watching the screen of the external display unit specifies a position corresponding to the display of the screen by using the input unit, the controller performs a control operation so as to reduce the distance between the specified point and the irradiation point of the spot light emitted from the tip of the manipulation tool (surgical tool). Therefore, the operator only needs to watch the screen of the external display unit. Not only the operator but also other members can watch the external display unit as well. The operator may sometimes turn away from the external display unit and check the surroundings. Thus, the operator can appropriately direct the team according to the surrounding situation.

The input unit serves as a user-interface for the operator to control the motion of the manipulation tool (surgical tool) at will by using the functions of the controller and driver.

Taking a surgery system as an example, an advantage of the remote control system according to the present invention over conventional surgery systems in terms of operability is hereinafter explained: In the conventional surgery system, the result of an operation performed through the operation input device is merely displayed as a motion of the surgical tool on the screen. On the other hand, according to the present invention, the result of an operation performed on the input unit is additionally presented on the screen. In the conventional surgery system, the result of an input operation performed by a practitioner through the operation input unit is immediately reflected on the actual motion of the surgical tool; therefore, the operation must be carefully performed. By contrast, in the case of the present invention, both the target point (specified point) for the motion of the surgical tool and the actual position of the tool are displayed on the screen; if the actual motion of the surgical tool has been found to be inappropriate, the operator can appropriately deal with the situation by changing the target point (specified point).

The present invention is applicable not only in the case where the operator performing the operation is near the object, but also in the case where the operator is remote from the object. In the latter case, at least the external display unit and input unit should be provided on the operator side (the operator side apparatus), whereas the imaging device, manipulation tool and driver should be provided on the object side (the object side apparatus). The distance calculator and controller may be provided either on the operator side apparatus or object side apparatus. The operator side apparatus and object side apparatus should be connected via a communication line such as a local area network (LAN) or the Internet. The communication line is used for transmitting image data from the imaging device to the external display unit, and for sending input information from the input unit to the driver (by way of the controller and distance calculator). Thus, the operator can perform operations on a remote object as if the object is at hand.

| | EXPLANATION OF NUMERALS |
|---|---|
| 11 | Surgical Tool (Tool) |
| 12 | Imaging Device (Endoscope) |
| 13 | Driver |
| 14 | Imaging Section |
| 15 | Controller |
| 16 | External Display Unit |
| 17 | Input Unit |
| 17a | Touch Panel |
| 17b | Mouse |
| 18 | Patient |
| 19 | Surgical Tool Insertion Hole |
| 21 | Patient Side Apparatus |
| 22 | Practitioner Side Apparatus |
| 23 | Internet |

BEST MODES FOR CARRYING OUT THE INVENTION

Figure 1:
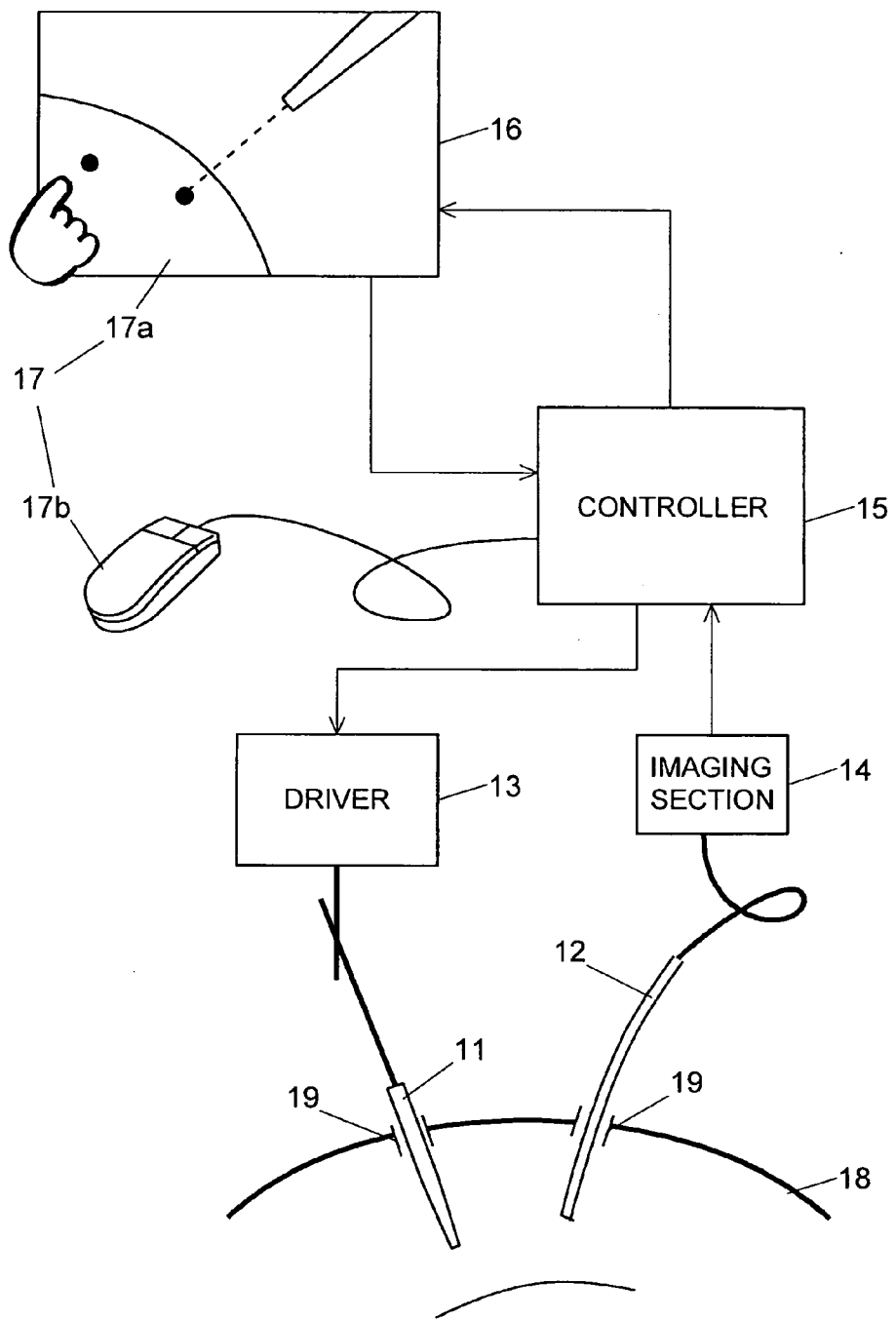
FIG. 1 is a schematic configuration diagram of a surgery system as the first mode of the present invention.

A surgery system which is the first mode of the remote control system according to the present invention is shown in FIG. 1. This system includes a rod-shaped surgical tool (manipulation tool) 11, imaging device 12, driver 13, imaging section 14, controller 15, external display unit 16 and input unit 17. The input unit in the present system includes a touch panel 17a mounted on the screen of the external display unit, a mouse 17b connected to the controller, a keyboard (not shown) and other devices. The surgical tool 11 and imaging device 12 are respectively inserted through the holes 19 into the body cavity of the patient 18. The surgical tool 11 can be driven to motions, such as rotation and backward and forward motions, by the driver 13. The imaging device 12 has its motion controlled by the imaging section 14. The images taken by the imaging device are converted into signals by the imaging section 14 and sent to the controller 15. The controller 15 displays, on the external display unit 16, the images taken by the imaging device 12. Meanwhile, based on the instructions provided through the input unit 17 by the practitioner, the controller operates the driver 13 to control the motion of and treatment by the surgical tool 11. For example, if the surgical tool 11 is a laser scalpel, the treatment by the surgical tool 11 may be by irradiation, resection, cut or cauterization with a laser beam. If the surgical tool 11 is an electrical knife, the treatment may be by resection, cut, cauterization, and so on.

An example of the operation of the present system is as follows. When a practitioner inserts the imaging device 12 into the patient's body, an image taken by the device is shown on the external display unit 16. Maintaining this state, the practitioner inserts the surgical tool 11 into the body and sets the driver 13 to enable the driving of the surgical tool 11 by the driver 13. Watching the screen of the external display unit 16, the practitioner specifies a target point on the touch panel 17a mounted on the screen. In response to this action, the controller 15 detects the difference in the position on the screen between the specified target point and the tip of the surgical tool 11, and computationally determines what motion of the surgical tool 11 is required to bring the tip of the surgical tool 11 closer to the target point. The computed result is sent to the driver 13, which accordingly controls the motion of the surgical tool 11. This control process brings the tip of the surgical tool 11 closer to the target point. After the tip has reached the target point, the practitioner instructs, on the touch panel 17a, what treatment should be performed by the surgical tool 11. Upon receiving this instruction, the controller 15 gives a command through the driver 13 to the surgical tool 11 to perform the operation as instructed. Thus, the practitioner can conduct a desired operation by simply giving instructions on the screen 16 while watching the same screen 16.

The previous explanation is completely applicable in the case where a mouse 17b is used as well as to the previous example where the touch panel 17a is used as the input unit 17; the mouse-based method also enables the practitioner to give instructions on the screen 16 while mainly watching the screen 16.

Figure 2:
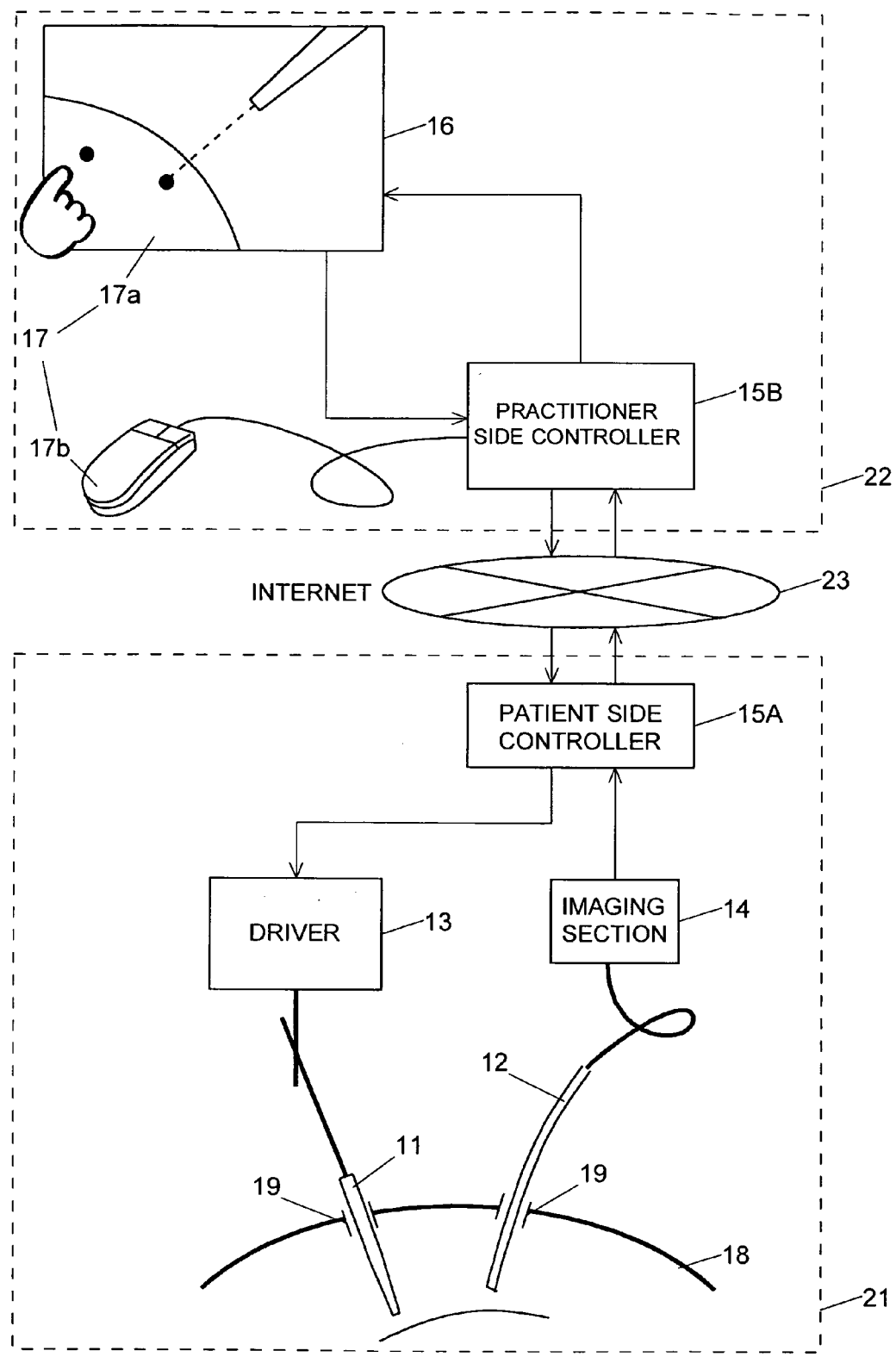
FIG. 2 is a schematic configuration diagram of a surgery system as the second mode of the present invention.

The second mode of the remote control system according to the present invention is shown in FIG. 2. The present system is designed to be used in the case where the practitioner is remote from the patient. Specifically, the system includes a patient side apparatus 21 provided on the patient side and a practitioner side apparatus 22 provided on the practitioner side. The patient side apparatus 21 includes the surgical tool 11, imaging device 12, driver 13, imaging section 14 and patient side controller 15A, which are all identical to those in the first mode system. The practitioner side apparatus 22 includes the external display unit 16 and input unit 17, which are both identical to those in the first mode system, and additionally a practitioner side controller 15B responsible for controlling these two units. The patient side apparatus 21 is connected to the practitioner side 22 via the Internet 23.

The configuration of the second mode system is identical to that of the first mode system except that communication lines (e.g. LANs and the Internet) are used to transmit information. Accordingly, the operation of the second mode system is basically the same as that of the first mode system. Therefore, the practitioner can perform operations on a remote patient as if the patient is located nearby.

Although the examples described thus far are both surgery systems, the present invention can naturally be applied to any remote control system other than the surgery system. For example, in the aforementioned case where an object is worked in an environment free from oxygen, water, dust and so on, the operator may place the object in a container from which the aforementioned substances have been removed, and then remotely manipulate a working tool from outside the container by using a system according to the present invention. The present invention allows the use of a relatively small container capable of containing the object and thereby reduces the cost to a level lower than in the case of using a clean room that requires huge costs for construction, maintenance and operation.

The remote control system according to the present invention may also be suitably used in the case where there is no partition such as a body wall or container. For example, if the object is too small to be visible to the unaided eye, or if a microstructure that cannot be checked with the unaided eye must be created, the present system can be used to display an enlarged image of the object or target site, on which image the operator can precisely specify the motion of the manipulation tool through the input unit. Thus, the work can be precisely performed.

Embodiment

Figure 3:
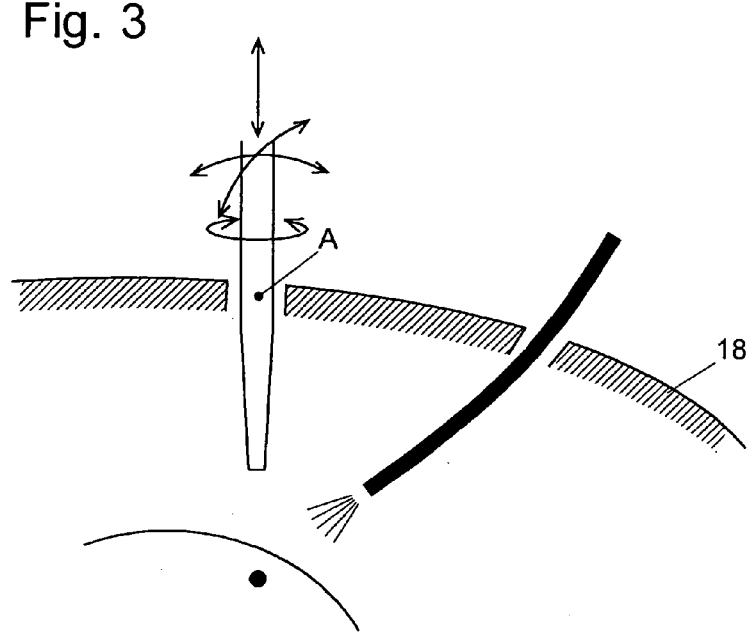
FIG. 3 is a schematic configuration diagram illustrating the relationship between the tool and the surgical object in an embodiment of the present invention.
Figure 4:
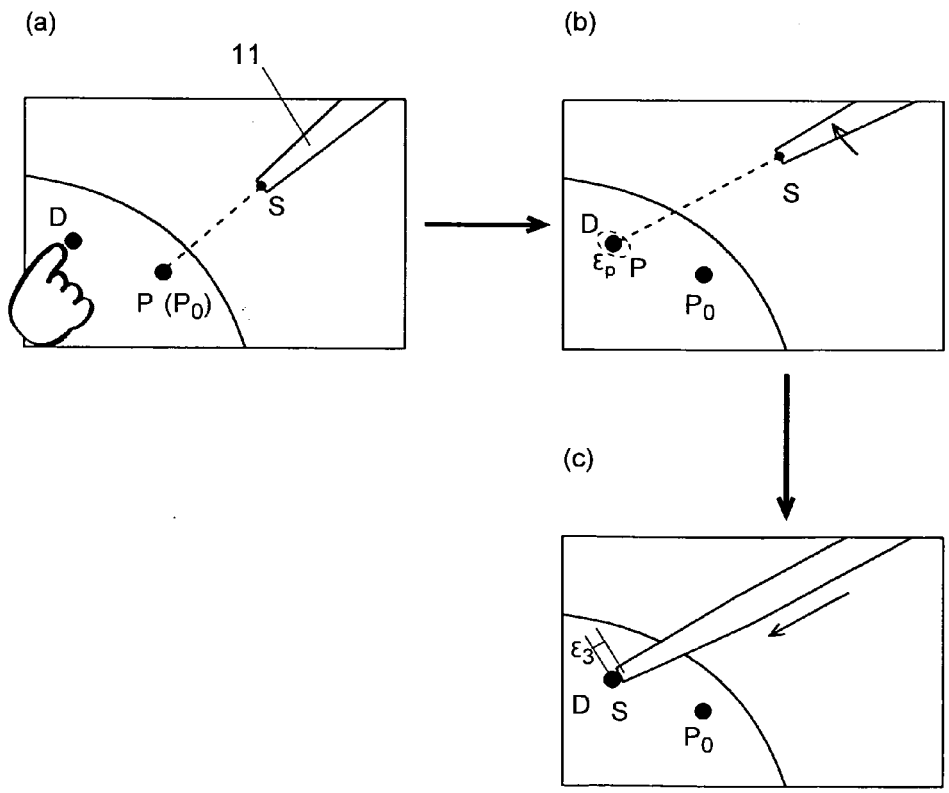
FIG. 4 is an illustration showing a method for driving the tool in the aforementioned embodiment.
Figure 5:
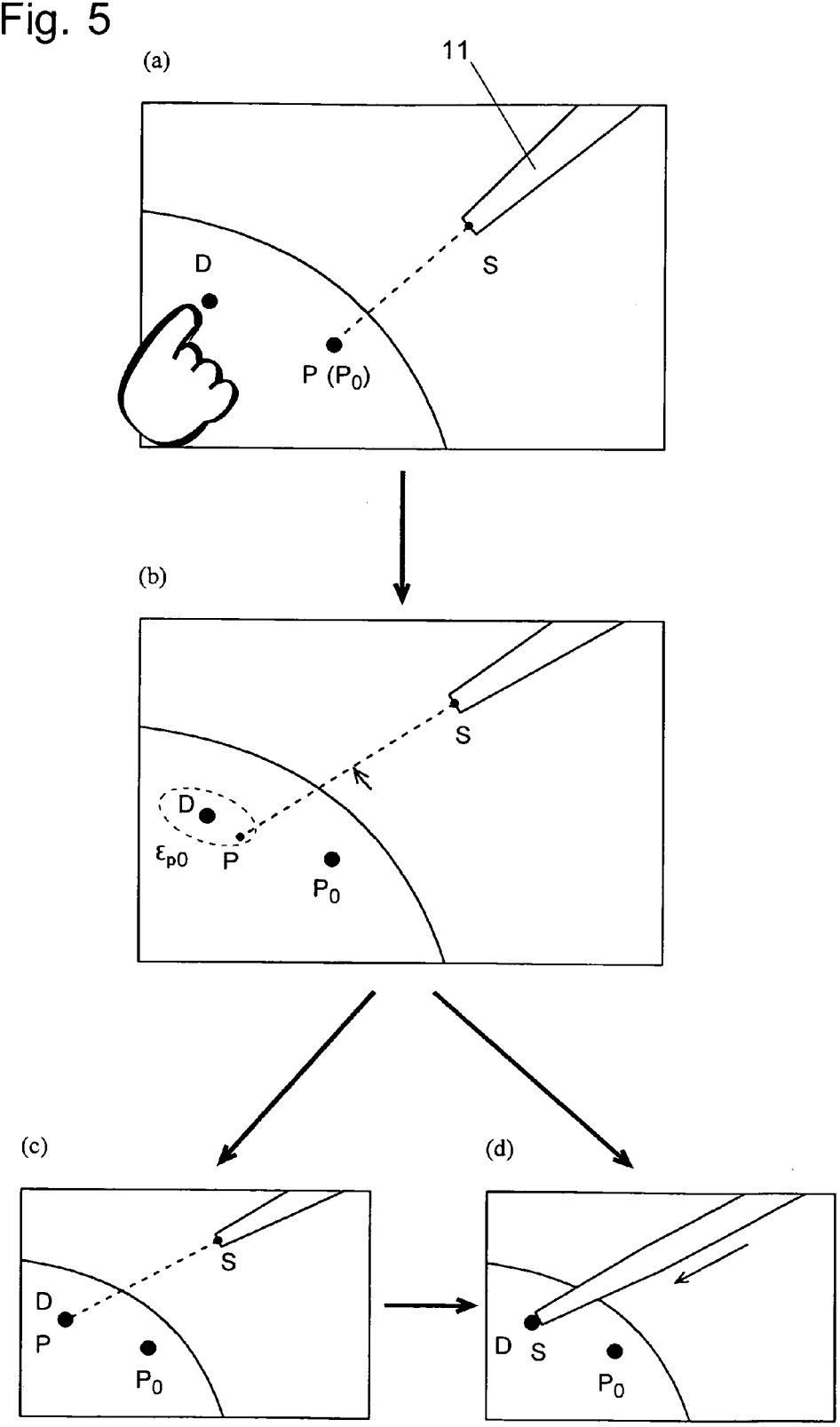
FIG. 5 is an illustration showing another method for driving the tool in the aforementioned embodiment.

A specific embodiment of the present invention is hereinafter described with reference to FIGS. 3 to 5. The basic configuration of the system in the present embodiment is identical to those of the surgery systems in the first and second modes of the present invention. The following description will explain the control process of the system in sequence, referring to the surgical tool as the "tool", the driver as the "robot", the imaging device as the "endoscope" and the external display unit as the "display."

[1] Problem Setting

An image displayed on the display includes three kinds of point coordinates as follows (FIG. 4(a)):

(1) Coordinates of a target point specified on the screen by an operator: $D(x_d, y_d)$
(2) Image coordinates of the tool's tip point: $S(x_s, y_s)$
(3) Image coordinates of the spot point of a laser attached to the tool 11: $P(x_p, y_p)$ It should be noted that, even if an operator specifies a target point on the screen, the three-dimensional coordinate of the corresponding object (within the body) cannot be determined since the depth-directional coordinate $z_d$ is indeterminable. Therefore, in this state, it is impossible to perform the three-dimensional positioning of the tool's tip to the target point.

Given this problem, a laser pointer (laser emitter) is attached to the tip of the tool 11 so that the tool's tip can be three-dimensionally positioned to the target point by bringing the spot point of the laser to the target point on the screen.

[2] Relationship Between Moving Velocity of Tool and Image Velocity of Laser Spot Point The tool 11 is held and controlled by the robot. As mentioned earlier, this tool 11 is inserted into a hole formed in the body surface (FIG. 3) and kinematically bound by the insertion point A. Therefore, it has four kinematic degrees of freedom as follows:

Two degrees of freedom for the spherical (rotational) motion around the insertion point A.
One degree of freedom for the rotation about the tool axis.
One degree of freedom for the translation along the tool axis.

Accordingly, the robot for controlling the tool 11 only needs to have four joints.

A process of controlling the velocity of the robot is hereinafter considered. Let $(\omega_x, \omega_y)$ denote the rotational velocity of the two degrees of freedom of the tool's tip around the insertion point A, $\omega_z$ the rotational velocity about the tool's axis, and $v_z$ the translational velocity along the tool's axis. Then, the laser spot point $P(x_p, y_p)$ is independent of $(\omega_z, v_z)$; it depends exclusively on $(\omega_x, \omega_y)$. According to these parameter settings, the image velocity of the laser spot point $P(x_p, y_p)$ is given by:

$$(\dot{x}_p, \dot{y}_p) = \left(\frac{dx_p}{dt}, \frac{dy_p}{dt}\right)$$

and this velocity is related to the rotational velocity $(\omega_x, \omega_y)$ of the tool's tip as follows:

$$\begin{pmatrix} \dot{x}_p \\ \dot{y}_p \end{pmatrix} = J \begin{pmatrix} \omega_x \\ \omega_y \end{pmatrix}$$

where J is an image Jacobian matrix, which can be expressed as follows:

$$J = \begin{pmatrix} J_{11} J_{12} \\ J_{21} J_{22} \end{pmatrix}$$

In general, a Jacobian matrix J changes depending on the parameters of the camera (endoscope), the positional relationship between the camera (endoscope) 12 and the tool 11, and the distance between the tool 11 and the target (laser spot point). However, the system in the present embodiment can be controlled with these values and relationship almost fixed. Therefore, J can be definitely determined by prior calibration, i.e. by previously calibrating the positional change of the laser spot point $P(x_p, y_p)$ with a change in the rotational velocity $(\omega_x, \omega_y)$ of the robot (or tool).

[3] Steps of Bringing Laser Spot Point $P(x_p, y_p)$ Closer to Target Point $D(x_d, y_d)$ The laser spot point $P(x_p, y_p)$ can be brought closer to the point $D(x_d, y_d)$ by moving the point $P(x_p, y_p)$ at the following image velocity:

$$\begin{pmatrix} k_1(x_d - x_p) \\ k_2(y_d - y_p) \end{pmatrix}$$

where $k_1, k_2 > 0$. This motion can be achieved by giving the following rotational velocity to the terminal device of the robot (or tool):

$$\begin{pmatrix} \omega_x \\ \omega_y \end{pmatrix} = J^{-1} \begin{pmatrix} k_1(x_d - x_p) \\ k_2(y_d - y_p) \end{pmatrix}$$

Accordingly, the entire process will include the following steps (1) through (4):

(1) Detect the laser spot point $P(x_p, y_p)$ by image processing.
(2) Calculate the rotational velocity $(\omega_x, \omega_y)$ of the robot (or tool) by the following equation:

$$\begin{pmatrix} \omega_x \\ \omega_y \end{pmatrix} = J^{-1} \begin{pmatrix} k_1(x_d - x_p) \\ k_2(y_d - y_p) \end{pmatrix}$$

(3) Control the angular velocity of each joint of the robot to realize the calculated rotational velocity $(\omega_x, \omega_y)$.
(4) Final Condition:
Calculate the distance between the laser spot point $P(x_p, y_p)$ and the target point $D(x_d, y_d)$ by the following equation:

$$d_{pd} = \sqrt{(x_d - x_p)^2 + (y_d - y_p)^2}$$

and discontinue the process if the distance has been equal to or smaller than a predetermined value $\epsilon_p$, i.e. if the following condition has been met (FIG. 4(d)):

$$d_{pd} < \epsilon_p$$

Otherwise, return to (1).

[4] Steps of Bringing Tool's Tip Point $S(x_p, y_p)$ Closer to Target Point $D(x_d, y_d)$ The point $S(x_s, y_s)$ can be brought closer to the target point $D(x_d, y_d)$ by pushing the tool into the body (i.e. translating the tool along its axis) at a velocity proportional to the distance between the two points given by the following equation:

$$d_{sd} = \sqrt{(x_d - x_s)^2 + (y_d - y_s)^2}$$

That is, the velocity can be expressed as $k_3 \cdot d_{sd}$ (where $k_3 > 0$).

Accordingly, similar to the previous case, the entire process will include the following steps (1) through (4):

(1) Detect the tool's tip point $S(x_s, y_s)$ by image processing.
(2) Calculate the translational velocity $v_z$ of the tool by the following equation:

$$v_z = k_3 d_{sd}$$

(3) Control the angular velocity of each joint of the robot to realize the calculated translational velocity $v_z$.

(4) Final Condition:

Discontinue the process if the following condition has been met (FIG. 4(c)):

$$d_{sd} < \epsilon_3$$

Otherwise, return to (1).

In the actual cases, the processes (motions) in [3] and [4] can be simultaneously performed (FIG. 5(b)→(c) and (d)) when the distance $d_{pd}$ between the laser spot point $P(x_p, y_p)$ and the target point $D(x_d, y_d)$ is equal to or smaller than a predetermined value $\epsilon_{p0}$ (where $\epsilon_{p0} > \epsilon_p$).

In the system according to the present invention, the tool's tip point S (and the laser spot point P) always follows the specified point D when the operator (practitioner) moves the point D on the screen after the tool's tip point S has reached the proximity of the target point D, while the tool's tip point S is approaching the target point D, or even while the laser spot point P is approaching the target point D. Meanwhile, the tool can be maintained in the operable state (i.e. in the state capable of irradiation, resection, cut, cauterization or other treatments). In this case, the practitioner can conduct the irradiation, resection, cut, cauterization or other treatments by simply specifying appropriate points on the screen.

[5] Configuration of Control Program

The program for controlling the tool (or robot) in the previously described manner can be composed of the following elements:

(1) Image processing part, including a (real-time) program for detecting the laser spot point $P(x_p, y_p)$ and the tool's tip point $S(x_s, y_s)$ from an image.

(2) Robot control part, including a program for controlling the angular velocity of each joint of the robot to realize the rotational and translational velocity ($\omega_x, \omega_y, \omega_z, v_z$) of the tool with the four degrees of freedom.

(3) Touch-panel user-interface part, including a user-interface for switching the operation between a target-point detection program, calibration process and online control process, and for setting parameters (every switching and setting can be done on a touch panel).

(4) A program for performing calibration to create a Jacobian matrix J.

(5) A control program for bringing the laser spot point $P(x_p, y_p)$ closer to the target point $D(x_d, y_d)$.

(6) A control program for bringing the tool's tip point $S(x_s, y_s)$ closer to the target point $D(x_d, y_d)$.

In the case of using a mouse as the input unit, the element (3) should be a "mouse user-interface part."

The present embodiment has assumed that the tool is bound by a hole and hence the kinematic degrees of freedom of the tool is four; if the tool is not bound by the hole, it is possible to perform the analysis on the assumption that the tool has five or more kinematic degrees of freedom, and manipulate the tool based on the analysis result. The present embodiment has also assumed that the robot has four joints in accordance with the kinematic degrees of freedom under the aforementioned conditions; however, it is naturally possible to provide either the robot or tool, or the two of them as a set, with a total of five or more joints.

The invention claimed is:

1. A remote control system for performing an operation on an object, comprising:
a) an imaging device that takes an image of the object;
b) a manipulation tool having, at a tip thereof, an illuminator that casts a spot light onto the object;
c) a driver that changes a position of the manipulation tool;
d) an external display unit that displays an image taken by the imaging device;
e) an input unit that allows an operator to specify a specified point corresponding to a display of the external display unit, the input unit being a device that allows the operator to input a trajectory, along which the tip of the manipulation tool is to follow the specified point, by moving the specified point on the display of the external display device;
f) a distance calculator that calculates a first distance, which is a distance between the specified point and a position of the spot light cast from the illuminator on the object, and that calculates a second distance, which is a distance between the specified point and the tip of the manipulation tool; and
g) a controller that controls the driver so as to simultaneously perform a process of bringing the position of the spot light closer to the specified point moving on the trajectory and a process of bringing the tip of the manipulation tool closer to the specified point moving on the trajectory, the controller having a function of controlling the driver so as to maintain a state where the first distance is equal to or smaller than a predetermined value when the specified point has been moved.

2. The remote control system according to claim 1, wherein the controller additionally rotates the manipulation tool about an axis thereof.

3. The remote control system according to claim 1, wherein the object is an affected area of a patient, and the manipulation tool is a surgical tool.

4. The remote control system according to claim 1, wherein the input unit is a touch panel mounted on the external display unit.

5. The remote control system according to claim 1, wherein the controller controls a motion of the manipulation tool by a velocity control.

6. The remote control system according to claim 1, wherein the controller has a function of controlling the manipulation tool so as to perform a predetermined operation on the object while the tip of the manipulation tool is moving.

7. The remote control system according to claim 6, wherein the predetermined operation is resection, cut or cauterization of the object or irradiation of the object with a laser beam.

8. A remote control system for performing an operation on an object located within a space beyond a partition, comprising:
a) an imaging device that takes an image of the object;
b) a rod-shaped manipulation tool having, at a tip thereof, an illuminator that casts a spot light, the manipulation tool being designed to be inserted through a hole provided in the partition;
c) a driver that changes a position of the manipulation tool;
d) an external display unit that displays an image taken by the imaging device;
e) an input unit that allows an operator to specify a specified point corresponding to a display of the external display unit, the input unit being a device that allows the operator to input a trajectory, along which the tip of the manipulation tool is to follow the specified point, by moving the specified point on the display of the external display device;
f) a distance calculator that calculates a first distance, which is a distance between the specified point and a position of the spot light cast from the illuminator on the object, and that calculates a second distance, which is a distance between the specified point and the tip of the manipulation tool; and g) a controller that controls the driver so as to simultaneously perform a process of bringing the position of the spot light closer to the specified point moving on the trajectory and a process of bringing the tip of the manipulation tool closer to the specified point moving on the trajectory, the controller having a function of controlling the driver so as to maintain a state where the first distance is equal to or smaller than a predetermined value when the specified point has been moved.

9. The remote control system according to claim 8, wherein the controller additionally rotates the manipulation tool about an axis thereof.

10. The remote control system according to claim 8, wherein a Jacobian matrix is used to convert information on the position of a spot on the image taken by the imaging device to a driving parameter relating to a rotation of the driver, and a motion of the manipulation tool is controlled by changing the driving parameter on the basis of the Jacobian matrix.

11. The remote control system according to claim 8, wherein the controller controls a motion of the manipulation tool by changing a driving parameter of the driver relating to forward and backward motions of the manipulation tool on the basis of information on a position of the tip of the manipulation tool on the image taken by the imaging device.

12. The remote control system according to claim 8, wherein:
the object is an affected area of a patient;
the partition is a body wall of the patient; and
the manipulation tool is a surgical tool.

13. The remote control system according to claim 8, wherein the input unit is a touch panel mounted on the external display unit.

14. The remote control system according to claim 8, wherein the controller controls a motion of the manipulation tool by a velocity control.

15. The remote control system according to claim 8, wherein the controller has a function of controlling the manipulation tool so as to perform a predetermined operation on the object while the tip of the manipulation tool is moving.

16. The remote control system according to claim 15, wherein the predetermined operation is resection, cut or cauterization of the object or irradiation of the object with a laser beam.

17. An operator side apparatus for a remote control system comprising:
an external display unit that displays an image taken by an imaging device;
an input unit that allows an operator to specify a specified point corresponding to a display of the external display unit, the input unit being a device that allows the operator to input a trajectory, along which a tip of a manipulation tool is to follow the specified point, by moving the specified point on the display of the external display device; and
a controller that controls a driver that changes a position of a manipulation tool so as to simultaneously perform a process of bringing a position of a spot light cast from an illuminator provided at the tip of the manipulation tool on an object closer to the specified point moving on the trajectory and a process of bringing the tip of the manipulation tool closer to the specified point moving on the trajectory, the controller having a function of controlling the driver so as to maintain a state where a first distance, which is a distance between the position specified by the input unit and the position of the spot light, is equal to or smaller than a predetermined value when the specified point has been moved.

18. An object side apparatus for a remote control system comprising:
an imaging device that takes an image of an object;
a manipulation tool having, at a tip thereof, an illuminator that casts a spot light onto the object;
a driver that changes a position of the manipulation tool, based on information provided by an input unit, the input unit being a device that allows an operator to input a trajectory, along which the tip of the manipulation tool is to follow a specified point, by moving the specified point on a display of an external display device; and
a controller that controls the driver so as to simultaneously perform a process of bringing a position of the spot light closer to the specified point moving on the trajectory by an input unit and a process of bringing the tip of the manipulation tool closer to the specified point moving on the trajectory, the controller having a function of controlling the driver so as to maintain a state where a first distance, which is a distance between the specified point and the position of the spot light, is equal to or smaller than a predetermined value when the specified point has been moved.

19. An operator side apparatus for a remote control system for performing an operation on an object located within a space beyond a partition, comprising:
an external display unit that displays an image taken by an imaging device;
an input unit that allows an operator to specify a specified point corresponding to a display of the external display unit, the input unit being a device that allows the operator to input a trajectory, along which a tip of a manipulation tool is to follow the specified point, by moving the specified point on the display of the external display device; and
a controller that controls a driver that changes a position of a manipulation tool so as to simultaneously perform a process of bringing a position of a spot light cast from an illuminator provided at a tip of the manipulation tool on the object closer to the specified point moving on the trajectory and a process of bringing the tip of the manipulation tool closer to the specified point moving on the trajectory, the manipulation tool being designed to be inserted through a hole provided in the partition, the controller having a function of controlling the driver so as to maintain a state where a first distance, which is a distance between the specified point by the input unit and the position of the spot light, is equal to or smaller than a predetermined value when the specified point has been moved.

20. An object side apparatus for a remote control system for performing an operation on an object located within a space beyond a partition, comprising:
an imaging device that takes an image of the object;
a manipulation tool having, at a tip thereof, an illuminator that casts a spot light onto the object, the manipulation tool being designed to be inserted through a hole provided in the partition;
a driver that changes a position of the manipulation tool, based on information provided by an input unit, the input unit being a device that allows an operator to input a trajectory, along which the tip of the manipulation tool is to follow a specified point, by moving the specified point on a display of an external display device; and
a controller that controls the driver so as to simultaneously perform a process of bringing a position of the spot light closer to the specified point moving on the trajectory by an input unit and a process of bringing the tip of the manipulation tool closer to the specified point moving on the trajectory, the controller having a function of controlling the driver so as to maintain a state where a first distance, which is a distance between the specified point and the position of the spot light, is equal to or smaller than a predetermined value when the specified point has been moved.

* * * * *